United States Patent

Muntwyler et al.

[11] 4,339,462
[45] Jul. 13, 1982

[54] ANTIMICROBIAL 3-HYDROXYDIPHENYL ETHERS

[75] Inventors: Rene' Muntwyler, Hofstetten; Kurt Burdeska, Basel, both of Switzerland

[73] Assignee: Ciba-Geigy Corporation, Ardsley, N.Y.

[21] Appl. No.: 214,295

[22] Filed: Dec. 8, 1980

Related U.S. Application Data

[62] Division of Ser. No. 960,697, Nov. 14, 1978, Pat. No. 4,268,693.

[30] Foreign Application Priority Data

Nov. 21, 1977 [LU] Luxembourg .................. 78554

[51] Int. Cl.$^3$ ........................................... A61K 31/09
[52] U.S. Cl. ................................... 424/341; 252/106; 252/107
[58] Field of Search ........................................... 424/341

[56] References Cited

U.S. PATENT DOCUMENTS 3,405,184 10/1968 Widiger et al. .................. 568/637
3,652,665 3/1972 Shen et al. .................. 568/637 X
3,904,696 9/1975 Model et al. .................. 568/637

OTHER PUBLICATIONS

Chemical Abstracts 46:8039h–8040a (1952).
Chemical Abstracts 71:112209x (1969).

Primary Examiner—Leonard Schenkman
Attorney, Agent, or Firm—Edward McC. Roberts

[57] ABSTRACT

3-Hydroxydiphenyl ethers of the formula

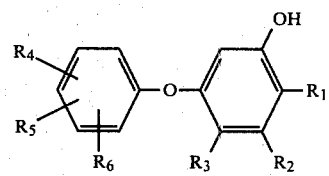

wherein $R_1$ represents hydrogen, fluorine or chlorine, each of $R_2$ and $R_3$ independently represents hydrogen or chlorine, and each of $R_4$, $R_5$ and $R_6$ independently represents hydrogen, fluorine, chlorine, bromine or alkyl of 1 to 4 carbon atoms, with the proviso that each phenyl nucleus contains at least one halogen atom, but the total number of halogen atoms in the molecule does not exceed 4, processes for their production and a method of using them for combating micro-organisms.

12 Claims, No Drawings

ANTIMICROBIAL 3-HYDROXYDIPHENYL ETHERS

This is a divisional of application Ser. No. 960,697 filed on Nov. 14, 1978, now U.S. Pat. No. 4,268,693.

The present invention provides novel halogenated 3-hydroxydiphenyl ethers, processes for their production, a method of using them for combating microorganisms, and compositions containing these compounds.

A variety of hydroxydiphenyl ethers are known from the literature, for example from Swiss Pat. No. 148,291, German Offenlegungsschrift Nos. 2,619,489 and 2,142,686 and U.S. Pat. No. 2,950,325. In particular, a great number of 2-hydroxydiphenyl ethers and their use as microbicides have been described, inter alia, in U.S. Pat. Nos. 3,506,720 and 3,629,477. The drawback of these 2-hydroxydiphenyl ethers is, however, that they are inactive against Pseudomonas bacteria (see for example U.S. Pat. No. 3,616,256). A number of halogenated 3-hydroxydiphenyl ethers are known from the following publications: German Pat. No. 628,792, U.S. Pat. No. 1,932,595, German Offenlegungsschrift No. 1,930,256 and J. Pharm. Soc. Japan 72 (1952), 478–82, reference in Chemical Abstracts, Vol. 47 (1953), 7082 b.

The present invention is based on the surprising observation that a specific group of halogenated 3-hydroxydiphenyl ethers has a particularly effective action against gram-positive and gram-negative bacteria and fungi and has a broader activity spectrum compared with the known halogenated hydroxydiphenyl ethers. Accordingly, the 3-hydroxydiphenyl ethers of the present invention, in contrast to the known bactericidal 2-hydroxydiphenyl ethers, also act against Pseudomonas bacteria. Furthermore, the 3-hydroxydiphenyl ethers of the invention are very advantageous from the ecological and toxicological standpoint.

The 3-hydroxydiphenyl ethers of the present invention have the formula

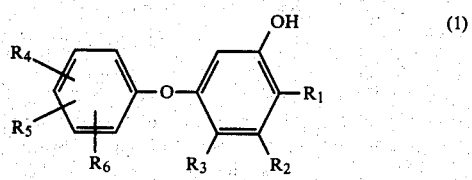

(1)

wherein $R_1$ represents hydrogen, fluorine or chlorine, each of $R_2$ and $R_3$ independently represents hydrogen or chlorine and each of $R_4$, $R_5$ and $R_6$ independently represents hydrogen, fluorine, chlorine, bromine or alkyl of 1 to 4 carbon atoms, with the proviso that each phenyl nucleus contains at least one halogen atom, but the total number of halogen atoms in the molecule does not exceed 4.

A preferred alkyl group $R_4$, $R_5$ or $R_6$ is the methyl group. The phenol ring preferably contains one halogen atom, and the phenyl ring contains preferably 1 or 2 halogen atoms.

Preferred compounds within the scope of the formula (1) are 3-hydroxydiphenyl ethers of the formula

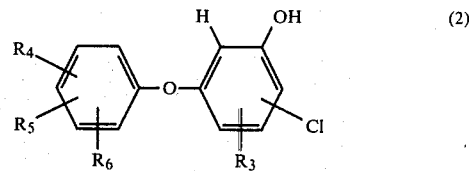

(2)

wherein $R_3$, $R_4$, $R_5$ and $R_6$ are as defined for formula (1), with the proviso that at least one of the substituents $R_4$, $R_5$ and $R_6$ represents a halogen atom, but the total number of halogen atoms in the molecule does not exceed 4, of which those compounds of the formula

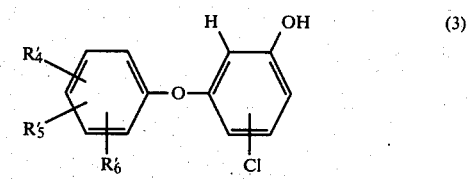

(3)

wherein each of $R_4'$, $R_5'$ and $R_6'$ independently represents hydrogen, fluorine, chlorine or methyl, with the proviso that at least one of these substituents represents a halogen atom, and of the formula

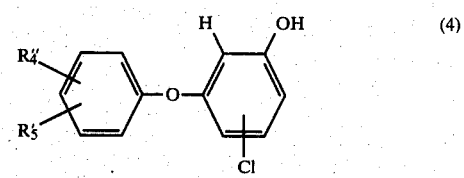

(4)

wherein $R_4''$ represents fluorine or chlorine and $R_5'$ represents hydrogen, fluorine, chlorine or methyl, and of the formula

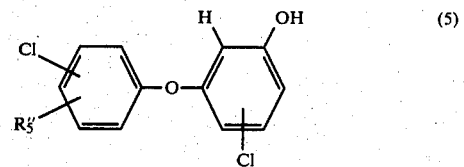

(5)

wherein $R_{5Q}''$ represents hydrogen, fluorine or chlorine, are of particular interest.

Particularly preferred compounds are 3-hydroxydiphenyl ethers of the formula

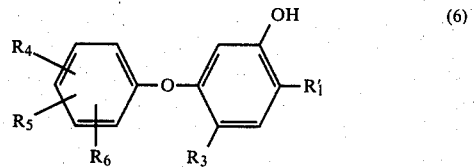

(6)

wherein $R_1'$ represents chlorine or fluorine, $R_3$ represents hydrogen or chlorine and $R_4$, $R_5$ and $R_6$ are as defined for formula (1), with the proviso that at least one of these three latter substituents represents a halogen atom, in particular those compounds of the formula

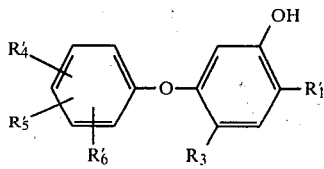

wherein $R_1'$ represents chlorine or fluorine, $R_3$ represents hydrogen or chlorine and each of $R_4'$, $R_5'$ and $R_6'$ independently represents hydrogen, fluorine, chlorine or methyl, with the proviso that at least one of these three latter substituents represents a halogen atom.

Preferred compounds within the group of compounds of the formula (7) are 3-hydroxydiphenyl ethers of the formula

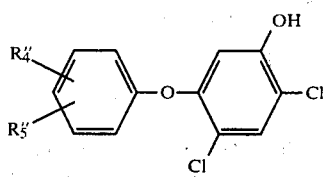

wherein $R_4''$ represents chlorine or fluorine and $R_5''$ represents hydrogen, fluorine or chlorine, and also those of the formula

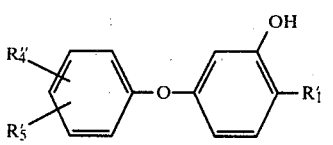

wherein each of $R_1'$ and $R_4''$ independently represents chlorine or fluorine and $R_5'$ represents hydrogen, fluorine, chlorine or methyl, especially those of the formula

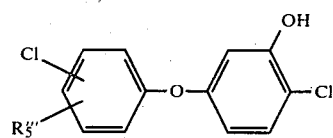

wherein $R_5'''$ represents hydrogen or chlorine.

The 3-hydroxydiphenyl ethers of the formulae (1) to (9) can be obtained by different processes which are in themselves known.

One such process for obtaining compounds of the formula (1) consists in demethylating an anisole of the formula

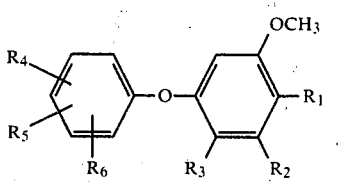

wherein $R_1$ to $R_6$ are as defined for formula (1), with the aid of an acid catalyst. The corresponding compounds of the formulae (2) to (9) can also be obtained starting from the correspondingly substituted anisoles.

Suitable acid catalysts for the demethylation (ether hydrolysis) are proton acids, for example hydrohalic acids, especially hydrobromic acid, or Lewis acids, for example $AlCl_3$ or $BF_3$. The reaction is carried out in an inert solvent [see L. Long et al., J. Org. Chem. 6 (1941), 852].

The starting compounds of the formula (10) can be obtained for example by the principle of the Ullmann reaction from an anisole of the formula

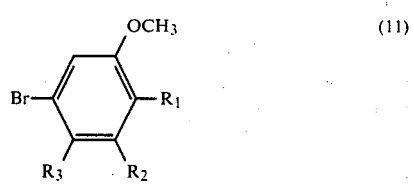

by condensation with a corresponding phenol of the formula

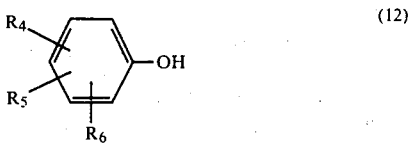

The reaction is carried out for example in the melt at 150° to 250° C. in boiling dimethyl acetamide or collidine (see R. G. R. Bacon et al., J. Chem. Soc. 1965, 4953). In formula (12), however, $R_4$, $R_5$ and $R_6$ should not be bromine, as otherwise secondary reactions occur.

The compounds of the formulae (11) and (12) are known or they can be obtained by methods which are in themselves known.

A further process for the production of 3-hydroxydiphenyl ethers of the formula

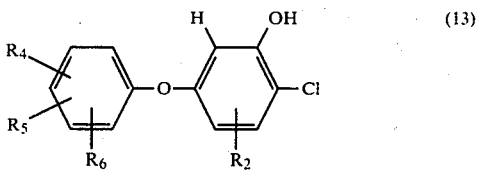

wherein $R_2$, $R_4$, $R_5$ and $R_6$ are as defined for formula (1), and thus also of the compounds of the formulae (6) to (9), in which $R_1'$ represents chlorine, comprises diazotising a compound of the formula

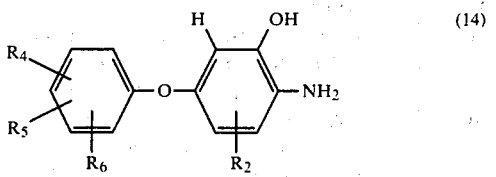

and converting the diazonium salt by the Sandmeyr reaction into the corresponding chlorine-substituted compound of the formula (13). The diazotisation can be carried out for example in the conventional manner with $NaNO_2$ in a strong mineral acid, whereupon the resulting diazonium salt is treated in an acid medium with CuCl [see T. Sandmeyr, B. 17 (1884), 2650].

The aminophenols of the formula (14) can be obtained by conventional reduction methods from the corresponding nitro compounds [see Brown et al., J. Phys. Chem. 32 (1928), 635], which in turn can be prepared by known methods, for example by the process disclosed in Swiss patent 505,781.

The starting materials of the formula (10), in which $R_1$ represents chlorine and $R_2$ and $R_3$ represent hydrogen, required for the first mentioned process, can also be obtained by the method just described from compounds of the formula

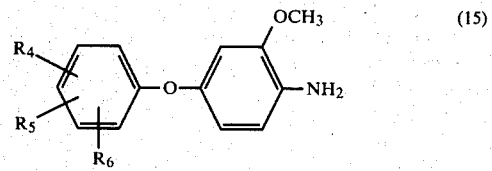  (15)

by diazotisation and subsequent Sandmeyr reaction (see Org. Synth. 1944, Coll. Vol. 2, 130).

Starting compounds of the formula (10), in which $R_1$ represents fluorine and $R_2$ and $R_3$ represent hydrogen, can be obtained by diazotisation of a compound of the formula (15) (for example in HCl with $NaNO_2$), precipitation in the form of the corresponding sparingly soluble tetrafluoroborate or hexafluorophosphate and subsequent Schiemann reaction [see Org. Reactions 1949, 193 and K. G. Rutherford et al., J. Org. Chem. 26 (1961), 5149], or direct by diazotisation of a compound of the formula (15) with $NaNO_2$ in HF [Van der Werf et al., J. Am. Chem. Soc. 70, (1948), 654].

The compounds of the formula (15) can be obtained from the corresponding nitro compounds by conventional reduction methods [e.g. W. Brown et al., J. Phys. Chem. 32 (1928), 635]. The nitro compounds can in turn be obtained by alkaline condensation from phenols of the formula (12) with the known 5-chloro-2-nitro-anisole [L. G. Raiford et al., J.Am. Chem. Soc. 48, (1926), 2652]; this condensation reaction can be carried out for example in dimethyl formamide with NaOH or KOH at temperatures between 80° and 170° C. or in an inert solvent, such as toluene, xylene, chlorobenzene or dichlorobenzene with aqueous NaOH or KOH, using a water separator. The alkaline condensation can also be carried out in a two-phase system consisting of aqueous NaOH or KOH and an inert solvent, such as toluene, xylene or chlorobenzene with the addition of a phase transfer catalyst.

3-Hydroxydiphenyl ethers of the present invention which contain a chloride atom in the para-position to the hydroxyl group, namely compounds of the formula

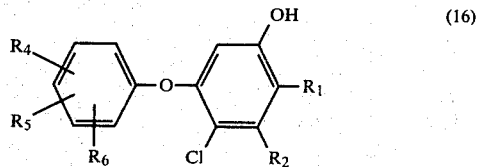  (16)

wherein $R_1$, $R_2$, $R_4$, $R_5$ and $R_6$ are as defined for formula (1), can also be obtained by chlorination of compounds of the formula

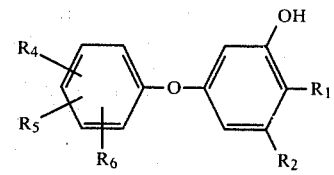  (17)

with sulfuryl chloride. In this manner it is possible to obtain preferably those compounds of the formulae (1) to (5), wherein the substituent in the para-position to the OH group is chlorine and the other positions of the phenol ring carry no substituents. The chlorination is carried out in an inert solvent, preferably in an ether, for example diethyl ether, preferably at elevated temperature, for example at the boiling point of the solvent employed [see P.P.T. Sah et al., J. Am. Chem. Soc. 63 (1941), 3164]. To increase the selectivity, the chlorination can be carried out in the presence of $AlCl_3$, advantageously with the addition of diphenyl sulfide (see W. D. Watson, Tetrahedron Letters 1976 (No. 30), 2591–2594). The starting compounds of the formula (17) can also be obtained by methods which are in themselves known, for example as described above for the production of 3-hydroxy-diphenyl ethers. A number of compounds of the formula (17), wherein $R_1$ and $R_2$ are hydrogen, which are not substituted in the phenol moiety can be obtained by reaction of compounds of the formula

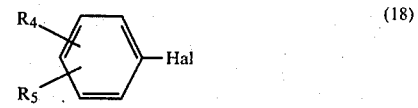  (18)

wherein Hal represents chlorine or bromine and $R_4$ and $R_5$ preferably represent hydrogen, fluorine or methyl or, in the 3- and 5-position, represent a hydrogen and chlorine atom or 2 chlorine atoms, in dimethyl formamide in the presence of an alkali metal hydroxide, with resorcinol, in the temperature range between 120° and 150° C. (see German Offenlegungsschrift 2,142,686).

A number of the 3-hydroxydiphenyl ethers of the present invention, for example those of the formula

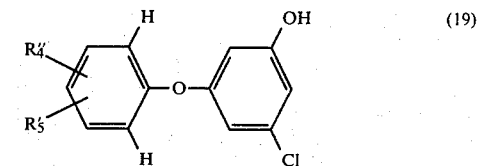  (19)

wherein $R_4''$ and $R_5'$ are as defined for formula (3) and formula (4) respectively, can also be obtained by reacting a phenolate of the formula

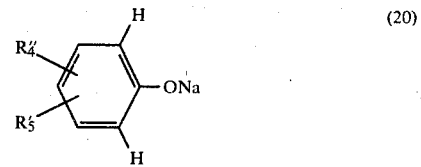  (20)

in the melt in the temperature range between 150° and 250° C., with 3,5-dichlorophenol using copper powder as catalyst. Thus in particular 3-hydroxy-5,3′,5′-trichlorodiphenyl ether can be obtained in this manner by reaction of sodium 3,5-dichlorophenolate with 3,5-dichlorophenol.

A number of the 3-hydroxydiphenyl ethers of the present invention, namely those of the formula

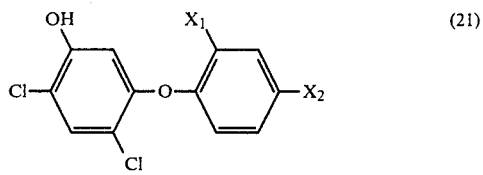

(21)

wherein one of the two substituents $X_1$ and $X_2$ represents chlorine and the other represents hydrogen or chlorine, can also advantageously be obtained by condensing 4,6-dichlororesorcinol with 1-nitro-4-chlorobenzene or 1-nitro-3,4-dichlorobenzene (or 1-nitro-2-chlorobenzene or 1-nitro-2,5-dichlorobenzene) in an alkaline medium, preferably with KOH, in a strongly polar solvent, for example dimethyl sulfoxide, reducing the resulting 3-hydroxy-4,6-dichloro-4′-(or 2′-)-nitrodiphenyl ether or 3-hydroxy-4,6-dichloro-4′-(or 2′-)-nitro-2′-(or 4′-)-chloro-diphenyl ether catalytically to produce the corresponding amino compound, using preferably Raney nickel as catalyst and dioxane as solvent, and diazotising the amino compound in conventional manner (e.g. with $NaNO_2$ in HCl solution) and treating the diazonium salt in an acid medium with CuCl (see T. Sandmeyr, B. 17 (1884), 2650).

The 4,6-dichlororesorcinol used as starting material can be prepared by the method of M. L. Morse et al., J. Am. Chem. Soc. 56, 2458.

The 3-hydroxydiphenyl esters of the formula (1) have good solubility in organic solvents and in propellant gases for aerosols. Their watersoluble salts, in particular the alkali metal and alkaline earth metal salts, are also effective and of particular importance where an application in aqueous medium and in soaps is contemplated.

Particular importance attaches to the compounds of the formula (1) on account of their broad antibacterial activity spectrum which embraces both gram-positive and gram-negative bacteria and fungi. With regard to the technical aspects of their use, the colourlessness and odourlessness of the compounds of the invention are of special value.

The antimicrobial compounds of the present invention can be used on a very broad basis, in particular for protecting organic substrates from attack by harmful and pathogenic micro-organisms. The antimicrobial agents are suitable accordingly as preservatives and disinfectants for industrial products of all kinds, as well as for deodorisation.

As examples of industrial products which can be preserved with the compounds of the invention, the following may be mentioned: adhesive substances, binding agents, paints, textile assistants and finishing agents, color pastes and printing pastes and similar preparations based on organic and inorganic dyestuffs and pigments, also those which contain casein or other organic compounds as admixtures. Wall and ceiling paints, for example those which contain an albuminous colour binder, are also protected from attack by pests by addition of the compounds according to the invention. Their use for protecting wood is also possible.

The compounds according to the invention can also be used as preservatives in the pulp and paper industry, inter alia for preventing the known formation of mucilage caused by micro-organisms in the apparatus used for manufacturing paper.

The action of the compounds according to the invention can also be utilised in providing plastics with preservative and disinfectant finishes. If plasticisers are used it is advantageous to add the antimicrobial agent to the plastic in the plasticiser in dissolved or dispersed form. It is expedient to ensure as uniform a distribution in the plastic as possible. The plastics with antimicrobial properties can be used for commodities of all kinds in which an activity against bacilli of the most diverse kinds, for example bacteria and fungi, is desired, thus for example for foot mats, bathroom curtains, seating accommodation, drip channel gratings in swimming baths and wall hangings. By incorporating the compounds according to the invention into corresponding wax compositions and floor polishing pastes there are obtained floor and furniture polishes with disinfectant action.

The compounds according to the invention can be used with advantage for providing fibres and textiles with a preservative and disinfectant finish. They can be applied to natural and synthetic fibres on which they exert a lasting action against harmful (also pathogenic) micro-organisms, for example fungi and bacteria. The compounds can be added before, simultaneously with, or after a treatment of these textiles with other substances, e.g. oil or printing pastes, flameproofing agents, fabric softeners, and other finishing agents. Textiles thus treated also have protection against perspiration odour caused by micro-organisms.

The forms in which the active substances according to the invention are applied generally correspond to the usual formulations. The agents used for the finishing or for the protection of textiles should contain the active substances in a finely divided form. In particular, solutions, dispersions and emulsions of the active substances are therefore used. Aqueous dispersions can be obtained, for example, from pastes or concentrates, and can be applied as liquids or in the aerosol form.

The aqueous solutions or dispersions advantageously contain surface-active agents; for example, anionic compounds such as soaps and other carboxylates (e.g. alkali metal salts of higher fatty acids), derivatives of sulfuroxyacids (e.g. sodium salt of dodecylbenzenesulfonic acid, watersoluble salts of sulfuric acid monoesters of higher molecular alcohols or of their polyglycol ethers, for example soluble salts of dodecyl alcohol sulfate or of dodecyl alcohol polyglycol ether sulfate), derivatives of phosphorus-oxyacids (e.g. phosphates), derivatives with acid (electrophilic) nitrogen in the hydrophilic group (e.g. disulfine salts), cationic surface-active agents, such as amines and their salts (e.g. lauryldiethylenetriamine), onium compounds, amine oxides or nonionic surface active agents, e.g. polyhydroxy compounds, surface-active agents based on mono- or polysaccharides, higher molecular weight acetylene glycols, polyglycol ethers (e.g. polyglycol ethers of higher fatty alcohols, polyglycol ethers of higher molecular weight alkylated phenols). In addition, the liquor can contain conventional adjuvants, for example watersoluble perborates, polyphosphates, carbonates, silicates, fluorescent brighteners, plasticisers, acid reacting salts, e.g. ammonium- or zincsilicofluoride, or certain organic acids, e.g. oxalic acid, also finishing agents, e.g. those based on synthetic resin or on starch.

The textile materials can be impregnated with the active substances, e.g. by means of hot or cold aqueous dyeing, bleaching, chroming or aftertreatment baths, whereby various textile-finishing processes are suitable, e.g. the padding or exhaustion process.

On account of their good solubility in organic solvents, the active substances are also suitable for application from non-aqueous media. The materials to be finished or preserved can moreover simply be impregnated with the solutions.

Suitable organic solvents are, for example, trichloroethylene, methylene chloride, hydrocarbons, propylene glycol, methoxyethanol, ethoxyethanol or dimethyl formamide, to which may also be added dispersing agents (e.g. emulsifiers, such as sulfated castor oil and fatty alcohol sulfates), and/or other adjuvants.

Depending on the purpose of application, the content of active substances according to the present invention can be, for example, between 0.1 and 50 g, preferably between 1 and 30 g, of active substance per liter of treatment liquid.

The active substances according to the present invention can be used on their own, or together with other known antimicrobial textile-preserving agents.

Suitable textiles to be finished or preserved are both fibres of natural origin, such as cellulose-containing fibres, e.g. cotton, or polypeptide-containing fibres, e.g. wool or silk, and fibre materials of synthetic origin, such as those based on polyamide, polyacrylonitrile or polyester, as well as blends of these fibres.

In general the textile materials are adequately preserved against infestation by fungi and bacteria by a content of 0.01 to 5%, preferably 0.1 to 3%, of active substance, based on the weight of the textile materials.

Detergents and cleansing agents having excellent antibacterial or antimycotic action are obtained by combining the compounds according to the invention with surface-active substances, especially with active detergents.

The detergents and cleansing agents can be in any desired form, e.g. in liquid, pasty, solid, flake or granular form. The compounds according to the invention can be incorporated into anionic compounds such as soaps and other carboxylates (e.g. alkali metal salts of higher fatty acids), derivatives of sulfuroxyacids (e.g. sodium salt of dodecylbenzenesulfonic acid, water-soluble salts of sulfuric acid monoesters of higher-molecular alcohols or of their polyglycol ethers, for example soluble salts of dodecyl alcohol sulfate or of dodecyl alcohol polyglycol ether sulfate), derivatives of phosphorus oxyacids (e.g. phosphates), derivatives with acid (electrophilic) nitrogen in the hydrophilic group (e.g. disulfine salts), as well as into cationic surface-active agents, such as amines and their salts (e.g. lauryldiethylenetriamine), onium compounds, amine oxides or nonionic surface-active agents, such as polyhydroxy compounds, surface-active agents based on mono- or polysaccharides, higher-molecular acetylene glycols, polyglycol ethers (e.g. polyglycol ethers of higher fatty alcohols, polyglycol ethers of higher-molecular alkylated phenols), or into mixtures of different surfactants. The antimicrobial activity of the new compounds is therewith completely retained. The active substance content of the detergents and cleansing agents, based on the weight of this agent, is generally from 0.01 to 5%, generally 0.1 to 3%. Aqueous preparations of such detergents and cleansing agents containing compounds according to the invention can be employed, for example, for the antimicrobial finishing of textile materials, since the active substance can be adsorbed substantively on to the textile material. They are also suitable as antimicrobial cleansing agents in the food manufacturing and bottling industries, e.g. in breweries, dairies, cheese dairies and slaughterhouses.

Furthermore, the compounds according to the invention can also be used in cosmetic preparations, e.g. volatile oils, bath salts, brilliantines, ointments, face lotions, hairdyeing preparations, hair oils, hair tonics, skin creams, skin oils, Eau-de-Cologne, perfumes, powders, rouge, depilatories, sun-ray filter creams and dental hygiene products, in consequence of which there is additionally imparted to these products an antimicrobial and deodorant action. In general, an active-substance content, based on the total weight of the product, of 0.01 to 5%, preferably of 0.1 to 3%, suffices. The compounds of the present invention are particularly suitable for use as active ingredients in disinfectant hand lotions.

For the purpose of disinfection and preservation, the compounds of formula (1) can also be used in combination with known antimicrobial agents. These include for example: phenol derivatives, such as 3,5-dichlorophenol, 2,5-dichlorophenol, 3,5-dibromophenol, 2,5-dibromophenol, 2,5-(or 3,5-)-dichloro-4-bromophenol, 3,4,5-trichlorophenol, 3,4,5-tribromophenol, phenylphenol, 4-chloro-2-phenylphenol, 4-chloro-2-benzylphenol, dichlorophene, hexachlorophene; aldehydes, such as formaldehyde, glutaraldehyde, salicylaldehyde; alcohols, such as phenoxyethanol; antimicrobial carboxylic acids and derivatives thereof; organometallic compounds, such as tributyl tin derivatives; iodine compounds, such as iodophors, iodonium compounds; quaternary ammonium compounds, such as benzyldimethyldodecylammonium chloride, dimethyldidecylammonium chloride, benzyl-di-(2-hydroxyethyl)-dodecylammonium chloride; sulfonium and phosphonium compounds; mercapto compounds and the alkali metal, alkaline earth metal and heavy metal salts thereof, such as 2-mercaptopyridine-N-oxide and the sodium and zinc salt thereof, 3-mercaptopyridazine-2-oxide, 2-mercaptoquinoxaline-1-oxide, 2-mercaptoquinoxaline-di-N-oxide, and also the symmetrical disulfides of these mercapto compounds; ureas, such as tribromocarbanilide or trichlorocarbanilide; dichlorotrifluoromethyldiphenylurea; tribromosalicylanilide; 2-bromo-2-nitro-1,3-dihydroxypropane; dichlorobenzoxazolone; chlorohexidine; isothiazolone and benzisothiazolone derivatives.

The applicability of compounds of formula (1) for combating micro-organisms, particularly bacteria and fungi, and for preserving organic materials and objects from infestation by micro-organisms, is very extensive. Thus, for example, they can be incorporated direct into the material to be preserved, e.g. into material having a synthetic resin base, such as polyamides and polyvinyl chloride, into paper-treatment liquors, into printing thickeners made from starch or cellulose derivatives, into lacquers and paints which contain, for example, casein, into cellulose, viscous spinning solutions, paper, into animal mucus or oils, into permanent coatings based on polyvinyl alcohol, cosmetic articles, and into ointments or powders. They can also be added to preparations of inorganic or organic pigments for the paint industry and to plasticisers.

The compounds of formula (1) can be used in the form of their organic solutions, e.g. as sprays, or as dry-cleaning agents, or for the impregnation of wood, suitable organic solvents being preferably solvents immiscible with water, particularly petroleum fractions, but also solvents miscible with water, such as $C_1$ to $C_6$ alcohols, e.g. methanol or ethanol or ethylene glycol monomethyl or monoethyl ether. Some of the compounds of this invention can be used also in aqueous solution.

Furthermore, the compounds can be used together with wetting or dispersing agents, in the form of their aqueous dispersions, e.g. for the preservation of substances which tend to rot, for example for the preservation of leather and paper, since the compounds undergo slight deactivation when combined with wetting agents and dispersants.

Solutions or dispersions of active substances, which can be used for the preservation of these materials, preferably have an active substance content of at least 0.005 g/liter, e.g. 0.01 to 5, preferably 0.1 to 3 g/liter.

The invention is illustrated by the following Examples, in which the parts and percentages are by weight unless otherwise stated.

EXAMPLE 1

42.8 g of 2-chloro-5-(4-chlorophenoxy)-anisole are dissolved in 370 g of glacial acetic acid and 260 g of 48% hydrogen bromide are added to the solution. The reaction mixture is heated for 24 hours to reflux temperature and, after cooling, is poured into 2000 ml of water. The product is extracted with toluene and the extract is repeatedly extracted with 2 N sodium hydroxide solution. The sodium hydroxide extracts are acidified with concentrated hydrochloric acid and extracted with toluene. Concentration of the toluene solution affords 34.6 g of a residual yellow oil which crystallises after a time and is further purified by recrystallisation from cyclohexane/hexane, affording 27.4 g of the compound of the formula

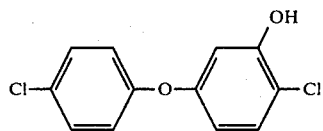 (101)

in the form of colourless crystals with a melting point of 69°–71° C.

The compounds of the following formulae are obtained in analogous manner using the correspondingly substituted anisoles as starting materials:

| | | |
|---|---|---|
| melting point 57 to 58° C. | 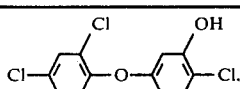 | (102) |
| melting point 46 to 48° C. | 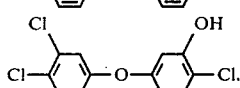 | (103) |
| boiling point (0.1 torr): 160° C. | 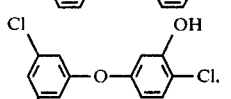 | (104) |
| boiling point (0.3 torr): 100 to 105° C. | 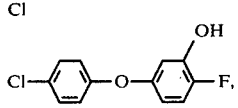 | (105) |
| boiling point (0.3 torr): 90 to 100° C. | 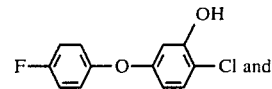 and | (106) |
| boiling point (0.3 torr): 100–102° C. | 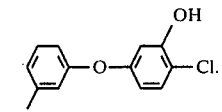 | (107) |

The 2-chloro-5-(4-chlorophenoxy)-anisole used as starting material can be prepared as follows:

(a) 169.8 g of 2-nitro-5-chloroanisole and 128.6 g of p-chlorophenol are dissolved in 700 ml of dimethyl sulfoxide. With stirring, 117 g of 50% potassium hydroxide solution are added dropwise at room temperature to the dimethyl sulfoxide solution in the course of ½ hour, whereupon the to operature of the mixture rises to 32° C. Stirring is continued for 1 to 2 hours, then the temperature is slowly raised to 90° C. and kept thereat for 2 hours. The reaction mixture is then stirred for 15 hours at 105° C., cooled and poured into ice-water. The precipitated crystal slurry is collected by suction and washed neutral, affording 242.4 g of brown crystals with a melting point of 69°–85° C.

Recrystallisation from alcohol yields 220 g of 2-nitro-5-(4-chlorophenoxy)-anisole in the form of yellow crystals with a melting point of 88°–89° C.

(b) 220 g of 2-nitro-5-(4-chlorophenoxy)-anisole are dissolved in 2000 ml of dioxane and, after addition of 20 g of Raney nickel, the solution is hydrogenated at room temperature and under normal pressure. The theoretical amount of hydrogen is taken up after 12 hours, whereupon the catalyst is filtered off and the solvent evaporated, affording as residue 196.5 g of 2-amino-5-(4-chlorophenoxy)-anisole in the form of a dark brown oil, which is further processed direct.

(c) 50 g of 2-amino-5-(4-chlorophenoxy)-anisole obtained in (b) are dissolved at 50° C. in 60 g of concentrated hydrochloric acid and 100 g of water. The solution is cooled to 15° C. and forms a viscous suspension. A solution of 13.8 g of sodium nitrite in 40 g of water is added dropwise in the course of ¼ hour at a temperature of +5° C. The reaction mixture is stirred for ½ hour at 5° C., and afterwards any excess nitrite is destroyed with sulfamic acid. The dark solution of the diazonium salt is freed from a small amount of undissolved substance and added dropwise in the course of 40 minutes to a solution of 65° C. of 10 g of copper(I) chloride in 200 g of concentrated hydrochloric acid. During the dropwise addition, the temperature is slowly raised to 95° C. The reaction mixture is stirred for 5 hours at 95° C. and then poured into 1000 ml of ice-water. The organic material is extracted with toluene and the extract is concentrated, affording as residue 50.7 g of 2-chloro-5-(4-chlorophenoxy)-anisole in the form of a black oil, which is used direct as starting material for the production of the compound of formula (101).

The starting materials for the compounds of formulae (102) to (107) can be obtained in analogous manner.

EXAMPLE 2

3.5 g of 6-amino-3-(2-chlorophenoxy)-phenol are dissolved at 70° C. in a solution of 20 g of concentrated hydrochloric acid, 20 g of water and 0.8 g of copper(I) chloride. With stirring, 10.2 g of sodium nitrite, dissolved in 8 g of water, are added dropwise to the hot solution of 70° C. in the course of 45 minutes. The reaction mixture is then stirred for 2 hours at 95° C. The cooled solution is poured into 100 ml of water and the organic material is extracted with toluene. Concentration of the toluene extract affords 3.3 g of a dark oil, which is distilled at 150° C. and 0.1 torr, yielding 2.1 g of the compound of the formula

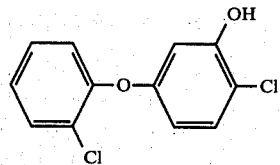
(201)

in the form of colourless crystals with a melting point of 67°–69° C.

EXAMPLE 3

3.45 g of 3-(2,4-dichlorophenoxy)-phenol are dissolved in 20 ml of diethyl ether and 1.22 ml of sulfuryl chloride are added dropwise to the solution at room temperature. The reaction mixture is heated for 15 hours to reflux temperature and then poured into ice-water. The product is extracted with diethyl ether and, after concentration of the extract, the residue is chromatographed on 80 g of silica gel with chloroform as eluant. Evaporation of the fractions, which analysis by thin layer chromatography shows to be unitary, yields 2.2 g of the compound of the formula

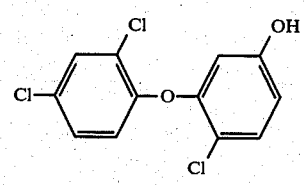
(301)

in the form of a colourless oil.

The compounds of the following formulae are obtained in analogous manner using 3-(4-chlorophenoxy)-phenol, 3-(3,4-dichlorophenoxy)-phenol or 3-(3,5-dichlorophenoxy)-phenol as starting materials:

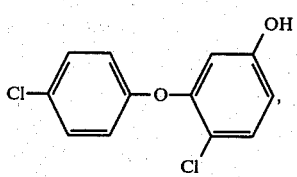
(302)

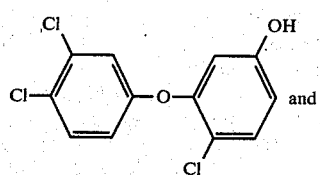
(303)

and

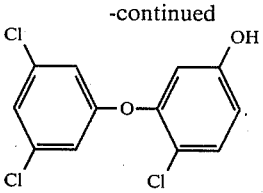
(304)

The 3-(2,4-dichlorophenoxy)-phenol used as starting material can be prepared as follows:

(a) 37.4 g of 3-bromanisole and 33.6 g of 2,4-dichlorophenol are dissolved in 400 ml of pyridine. After addition of a powdered mixture of 13.8 g of anhydrous potassium carbonate, 2 g of copper iodide and 2 g of copper powder, the reaction mixture is heated in an autoclave for 2 days to 160° C. with stirring. The cooled mixture is poured into water and extracted with toluene. The toluene extract is washed with 2 N sodium hydroxide solution, then with 2 N hydrochloric acid and finally with water, and then concentrated. The residue is distilled in vacuo. The main fraction distills at 125° to 135° C. (0.1 torr) and consists of 30 g of 3-(2,4-dichlorophenoxy)-anisole in the form of a colourless oil.

(b) 18.8 g of 3-(2,4-dichlorophenoxy)-anisole are added to a suspension of 37 g of anhydrous aluminium chloride in 80 ml of chlorobenzene and the mixture is stirred for 1 day at 60° C. The still hot solution is poured onto ice. The resulting mixture is extracted with toluene and the toluene solution is extracted with 2 N sodium hydroxide solution. The product is precipitated by acidifying the sodium hydroxide solution with dilute hydrochloric acid and extracted with toluene. The toluene solution is concentrated and the residue distilled in vacuo, affording 16 g of 3-(2,4-dichlorophenoxy)-phenol in the form of a colourless oil with a boiling point of 140°–145° C./0.05 torr. Using the corresponding chlorophenols as starting materials, it is possible to obtain the starting materials required for the production of the compounds of the formulae (302) to (304):

3-(4-chlorophenoxy)-phenol (boiling point: 145° C. at 0.1 torr), 3-(3,4-dichlorophenoxy)-phenol (boiling point: 135°–140° C. at 0.03 torr), 3-(3,5-dichlorophenoxy)-phenol (boiling point: 140° to 142° C. at 0.06 torr).

EXAMPLE 4

The chlorination procedure described in Example 3 is repeated using an equivalent amount of each of the compounds of the formulae (101), (102), (103), (107) or (201) instead of 3-(2,4-dichlorophenoxy)-phenol, yielding the compounds of the formulae

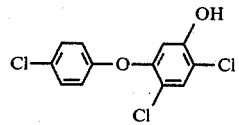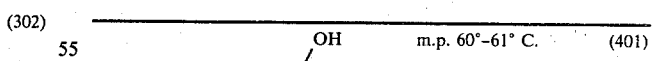 m.p. 60°–61° C. (401)

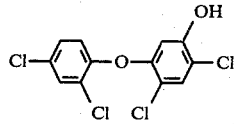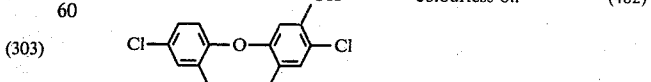 colourless oil (402)

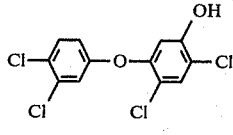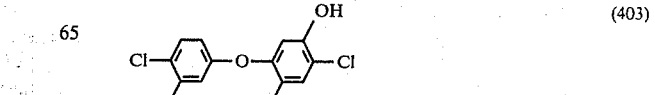 (403)

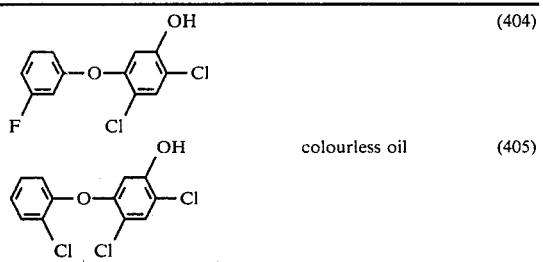

(404)

(405) colourless oil

EXAMPLE 5

32.6 g of 3,5-dichlorophenol, 37 g of sodium 3,5-dichlorophenolate and 4 g of copper powder are mixed and ground to a fine powder. The mixture is heated for 4 hours to 180° C. in a bomb tube. The solidified melt is dissolved in chloroform, filtered clear and concentrated. The residue is distilled in vacuo and 20 g of a unitary fraction in the form of a faintly yellowish oil are obtained at 168° C./0.3 torr. For purification, this oil is chromatographed on 500 g of silica gel with chloroform. Concentration of the fractions, which thin-layer chromatography shows to be unitary, yields 12.6 g of the compound of the formula

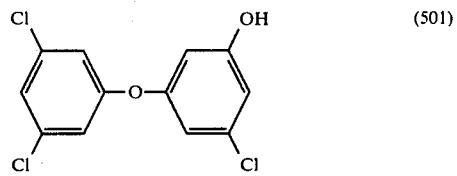

(501)

in the form of a colourless oil.

EXAMPLE 6

The compounds of the formulae (101) to (107), (201), (301) to (304), (401) to (405) and (501) are dissolved in an appropriate formulation (methyl cellosolve/-dimethyl formamide). The formulations are incorporated in a nutrient agar solution and the inhibition of the growth of microorganisms is determined by the gradient plate test.

Test Micro-organisms

*Staph. aureus* 511
*Staph. aureus* ATCC 6538
*Staph. aureus* K 322
*Strept. faecalis* ATCC 6055
*Strept. pyogenes* K 1129
*Corynebacterium bovis* ATCC 7715
*Lactobac. acidophilus* ATCC 4913
*Lactobac. acidophilus* ATCC 4356
Lactobacillus CRA
*Clostr. perfringens* LA 936
*Clostr. sporogenes* ATCC 3584
Clostridium CRA
*Bacteroides fragilis* ATCC 8482
*Bacteroides hypermegas* ATCC 25560
Bacteroides CRA
*Escherichia coli* ATCC 11229
*Escherichia coli* 0-580
*Escherichia coli* K 1075
*Proteus vulgaris* ATCC 6896
*Proteus mirabilis* NCTC 8309
*Salmonella gallinarum* SG 9
*Salmonella typhimurium* 1127
*Serratia marcescens* ATCC 13880
*Enterobacter aerogenes* ATCC 13048
*Pseudomonas aeruginosa* ATCC 15442
*Pseudomonas aeruginosa* K 1119
*Candida albicans* ATCC 10259
*Trich. mentagrophytes* ATCC 9533
*Aspergillus niger* ATCC 6275

GRADIENT PLATE TEST

The test plates are prepared according to the scheme

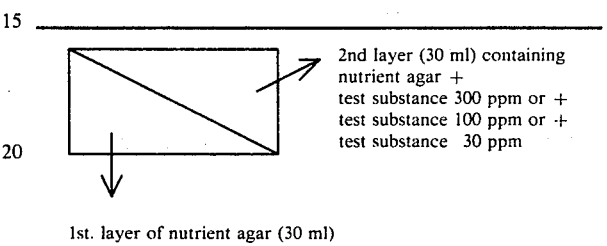

2nd layer (30 ml) containing
nutrient agar +
test substance 300 ppm or +
test substance 100 ppm or +
test substance 30 ppm 1st. layer of nutrient agar (30 ml)

The gradient plates are dried in a circulating air incubator.

The plates are inoculated with organisms or spore suspensions by application of a germ band with a capillary pipette in the direction of the concentration gradient (see scheme).

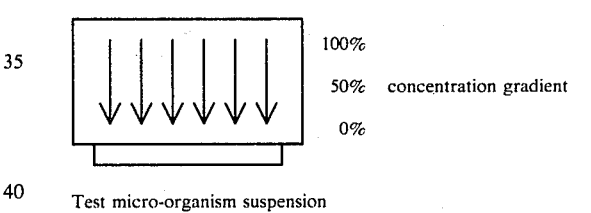

100%
50% concentration gradient
0%

Test micro-organism suspension

The plates, inoculated with bacteria and fungi, are incubated for 24 to 36 hours at 37° C.
Nutrient medium for bacteria: nutrient agar
Nutrient medium for fungi: Sabourad-Maltose agar
The tested compounds exhibit a good action against the bacteria and fungi used.

EXAMPLE 7

The compounds of the formulae (101) to (107), (201), (301) to (304), (401) to (405) and (501) are incorporated together with soap into a nutrient medium and the activity is determined according to the Agar Incorporation Test. The test micro-organisms are those used in Example 6.
Nutrient medium for bacteria: tryptone-glucose-extract-agar
nutrient medium for fungi: mycophil agar.
A 0.5% solution is prepared with sterilised water from a base soap mass. Sufficient of this stock solution is given to hot, sterile, liquid agar so that the nutrient medium contains 500 ppm of soap.

The test substances are dissolved in dimethyl sulfoxide, content 500 ppm. The active substance solution is put into sterilised Petri dishes in amounts of 0.1, 0.05 and 0.01 ml and treated and thoroughly mixed with 10 ml of nutrient medium which contains 500 ppm of soap (thus 5, 2.5 and 0.5 ppm are mixed in the nutrient medium).

After the plates have congealed the micro-organism suspensions are dropped thereon with a Pasteur pipette or with an inoculation device. Bacteria are incubated for 24 hours at 37° C. and fungi are incubated for 5 days at 28° C. Thereafter, it is determined whether the bacilli have grown or not. The compounds tested in this manner exhibit good activity against the micro-organisms used.

EXAMPLE 8

The compounds of the formulae (101) to (107), (201), (301) to (304), (401) to (405) and (501) are dissolved in a suitable formulation (ethyl cellosolve/dimethyl formamide).

The three substrates listed below are put into the solution baths and subsequently squeezed out between 2 aluminium sheets. The substrates are then dried in the air. The squeezing is carried out in such a way that (a) 2500 ppm, (b) 250 ppm or (c) 25 ppm of active substance are present on the fabric.

1. Reinforced cotton, causticized, bleached, weight per m$^2$: 121 g
2. Polyamide, nylon staple fabric, fixed, bleached, weight per m$^2$: 140 g.
3. Polyester, "Dacron" [Registered Trade Mark] staple fabric, type 54, fixed, bleached, weight per m$^2$: 130 g.

The substrates are then tested against the following 7 test organisms according to the agar diffusion test (modified AATC test method 90, 1970):

Bacteria

*Staphylococcus aures* ATCC 6538
*Escherichia coli* NCTC 8196
*Proteus mirabilis* NCTC 8309
*Pseudomonas aeruginosa* NCTC 8060

Fungi

*Candida albicans* ATCC 10'259
*Trichophyton mentagrophytes* ATCC 9533
*Aspergillus niger* ATCC 6275

The test plates consist of a twin layer agar, i.e. of a base layer of uninoculated nutrient agar and a surface layer of inoculated nutrient agar.

Bacteria: nutrient agar Fungi: mycophil agar

The filtered micro-organism suspension is poured on a congealed base layer and after the inoculated layer has congealed, discs of the respective substrates of 20 mm diameter are placed on the treated substrates. The bacteria and candida plates are incubated for 24 hours at 37° C.; the fungi plates are incubated for 3 to 5 days at 28° C. After the incubation the plates are evaluated for inhibition zones. If there are no inhibition zones, the growth beneath the test samples is examined under a magnifying glass.

The compounds tested in this manner exhibit, in conjunction with the substrates employed, good action against the above bacteria and fungi.

EXAMPLE 9

Crude paper which consists of 90% of bleached sulfite cellulose and 10% of birch is impregnated in a sizing press with a 2.5% solution of each of the compounds of the formulae (101) to (107), (201), (301) to (304), (401) to (405) or (501) in methanol/water (2:1) to a pickup of 40%. The dried paper contains 1% of active substance, based on its own weight.

To test the action against bacteria, discs of the impregnated paper measuring 10 mm in diameter are laid on brain heart infusion agar plates which have been inoculated beforehand with *Staphylococcus aureus*. The plates are then incubated for 24 hours at 37° C. To test the action against fungi, paper discs of 25 mm diameter are laid on mycophil agar plates and then inoculated with *Aspergillus niger*. The plates are then incubated for 72 hours at 30° C. On the one hand, the inhibition zones (IZ in mm) occurring around the paper discs are evaluated, and, on the other, the growth which can be determined microscopically (G in %) beneath or on the discs. The tested compounds exhibit good action against the bacteria employed.

EXAMPLE 10

A sample of 140 g of cotton/poplin is impregnated at 20° C. for 7 minutes in a bath of the following composition:
1000 ml of water
2.7 ml of an after-rinse liquor (containing 7% of a mixture of di-octadecyl- and di-hexadecyldimethylammonium chloride)
15 mg of one of the compounds of the formulae (101) to (107), (201), (301) to (304), (401) to (405) or (501).

The treated fabric sample is squeezed out to a pick-up of 100% and then dried at 45° C.

To test the action against bacteria, discs of the impregnated fabric measuring 25 mm in diameter are laid on brain heart infusion agar plates which have been inoculated with *Staphylococcus aureus*. The plates are incubated for 24 hours at 37° C. No growth of the test bacteria was observed beneath the disc.

EXAMPLE 11

To produce an antimicrobial bar of soap, 2.4 g of one of the compounds of the formulae (101) to (107), (201), (301) to (304), (401 to 405) or (501) are added to the following mixture:
120 g of base soap in flake form,
0.12 g of the disodium salt of ethylenediaminetetraacetic acid (dihydrate),
0.24 g of titanium dioxide.

The soap chips obtained by rolling are pulverised with an impeller and subsequently pressed.

Concentrated aqueous solutions of the antimicrobial bars of soap are mixed with brain heart infusion agar so as to give incorporation dilution series of 2, 10, 20, 100 etc. ppm of active substance. The warm mixtures are poured into Petri dishes, allowed to congeal and then inoculated with *Staphylococcus aureus*. The minimum inhibitory concentration is determined after incubation for 24 hours at 37° C. The tested compounds exhibit good action against the bacteria employed.

EXAMPLE 12

The following mixture is rolled for 20 minutes at 150° C. on a two roll mill:
100 g of polyvinyl chloride,
19.20 g of di-(2-ethylhexylphthalate),
27 g of di-(2-ethylhexylsebacate),
1.50 g of Ba/Cd laurate,
0.25 g of stearic acid
3.10 g of one of the compounds of the formulae (101) to (107), (201), (301) to (304), (401) to (405) or (501).

The roller nip is adjusted such that 1 mm rough sheets are produced. These sheets are then pressed for 20 minutes at 165° to 170° C. with a pressure of 1400 kg/cm².

To test the action against bacteria, round pieces measuring 10 mm in diameter are punched from the rolled plasticised polyvinyl chloride and laid on brain heart infusion agar plates which have been inoculated beforehand with *Staphylococcus aureus*. The plates are then incubated for 24 hours at 37° C. No growth of the test bacteria was observed beneath the discs.

EXAMPLE 13

A solution of 3 g of a compound of the formula (101) to (107), (201), (301) to (304), (401) to (405) or (501) and 3 g of sodium sulforicinoleate in 47 g of polyethylene glycol 400, and a solution of 7 g of sodium dodecylsulfate in 39.85 g of water are prepared. The two solutions are mixed and 0.15 g of perfume is added, yielding a very effective disinfectant hand lotion which is dropped or sprayed and rubbed onto the moist skin.

What is claimed is:

1. A method of combating micro-organisms on or in organic or inorganic material and of protecting said material from micro-organisms, which comprises incorporating in said material or applying to the surface thereof a microbiocidally effective amount of at least one compound of the formula

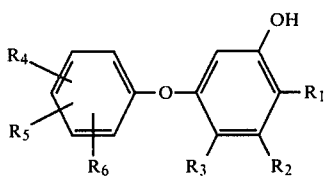

wherein $R_1$ represents hydrogen, fluorine or chlorine, each of $R_2$ and $R_3$ independently represents hydrogen or chlorine, and each of $R_4$, $R_5$ and $R_6$ independently represents hydrogen, fluorine, chlorine or bromine, with the proviso that each phenyl nucleus contains at least one halogen atom, but the total number of halogen atoms in the molecule does not exceed 4.

2. A method according to claim 1 wherein the organic material is textile material made of synthetic man-made fibres, regenerated man-made fibres or natural fibres.

3. A method according to claim 1 of disinfecting laundry goods and of protecting them from attack by micro-organisms, which comprises treating textiles with liquors which contain at least one of the compounds defined in claim 1.

4. A method according to claim 1 of protecting non-textile plastics material from attack by micro-organisms, which comprises incorporating in said plastics material, in any phase of the processing, or also in the monomers before the polymerisation, at least one of the compounds defined in claim 1.

5. A method according to claim 1 for protecting technical formulations, especially formulations of dyes, pigments, textile assistants, binders, sizes and paints, from attack by micro-organisms, which comprises incorporating therein at least one of the compounds defined in claim 1.

6. A method according to claim 1 for protecting paper from attack by micro-organisms, which comprises incorporating in the pulp at least one of the compounds defined in claim 1.

7. A method according to claim 1 for protecting cosmetic preparations, especially toilet requisites, such as soaps, deodorant sprays, powders and ointments, from attack by micro-organisms, which comprises incorporating in said preparations, in any phase of their manufacture, at least one of the compounds defined in claim 1.

8. A composition for combatting harmful micro-organisms which contains, as active ingredient, a microbiocidally effective amount of at least one compound of the formula

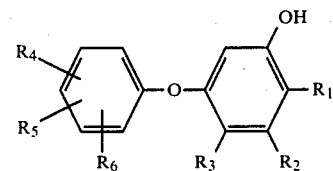

wherein $R_1$ represents hydrogen, fluorine or chlorine, each of $R_2$ and $R_3$ independently represents hydrogen or chlorine, each each of $R_4$, $R_5$, and $R_6$ independently represents hydrogen, fluorine, chlorine or bromine, with the proviso that each phenyl nucleus contains at least one halogen atom, but the total number of halogen atoms in the molecule does not exceed 4, and a suitable carrier therefor.

9. A composition with disinfectant action according to claim 8, which, in addition to the active ingredient, contains at least one of the following adjuvants as solid or liquid carrier: a soap, a surfactant, a foaming agent, an emulsifier, a dispersant or wetting agent, water, an organic solvent, a light stabiliser, a fluorescent whitening agent or another microbicidal substance.

10. A composition according to claim 8 for protecting non-textile plastics material as well as fibrous material made of natural and synthetic fibres from attack by and damage from micro-organisms, which contains as active ingredient a microbiocidally effective amount of at least one of the compounds defined in claim 1 and a suitable carrier therefor.

11. A composition according to claim 8 for personal hygiene with disinfectant and deodorant action which contains, as active ingredient, a microbiocidally effective amount of at least one of the compounds defined in claim 1 and a suitable carrier therefor.

12. An antimicrobial soap according to claim 11 which contains 0.01 to 5% of said active ingredient.

* * * * *